US00PP36085P2

(12) United States Plant Patent
Xiangang et al.

(10) Patent No.: US PP36,085 P2
(45) Date of Patent: Aug. 27, 2024

(54) ***HOYA COMMUTATA* PLANT NAMED 'Jingfeng Variegata'**

(50) Latin Name: *Hoya commutata*
Varietal Denomination: Jingfeng Variegata

(71) Applicant: Anhui Jadeite Garden Co., Ltd, Chuzhou (CN)

(72) Inventors: Shen Xiangang, Chuzhou (CN); Wang Dongliang, Chuzhou (CN); Gou Yunxia, Chuzhou (CN)

(73) Assignee: Anhui Jadeite Garden Co., Ltd (CN)

( * ) Notice: Subject to any disclaimer, the term of this patent is extended or adjusted under 35 U.S.C. 154(b) by 0 days.

(21) Appl. No.: 18/372,195

(22) Filed: Sep. 25, 2023

(51) Int. Cl.
*A01H 5/02* (2018.01)
*A01H 6/08* (2018.01)

(52) U.S. Cl.
USPC ..... Plt./380
CPC ..... *A01H 6/08* (2018.05)

(58) Field of Classification Search
USPC ..... Plt./380
CPC ..... A01H 6/08; A01H 5/02
See application file for complete search history.

*Primary Examiner* — Keith O. Robinson
(74) *Attorney, Agent, or Firm* — Cassandra Bright

(57) ABSTRACT

A new and distinct *Hoya* plant named 'JINGFENG VARIEGATA' is disclosed, characterized by glossy, undulated variegated foliage which has been proven stable. Foliage is dark green with a large light yellow center. The new variety is a *Hoya*, typically produced as an indoor ornamental plant.

4 Drawing Sheets

Latin name of the genus and species: *Hoya commutata.* Variety denomination: 'Jingfeng Variegata'.

BACKGROUND OF THE INVENTION

The new cultivar is a product of a spontaneous mutation. The new variety was discovered by the inventors in an existing population of unnamed, unpatented plants of *Hoya commutata* in September 2019 at a nursery in Chuzhou, China.

Asexual reproduction of the new cultivar 'JINGFENG VARIEGATA' was first performed in Chuzhou, China by terminal vegetative cuttings in 2020. Subsequent propagation has shown that the unique features of this cultivar are stable and reproduced true to type.

The following traits have been repeatedly observed and are determined to be the unique characteristics of 'JINGFENG VARIEGATA.' These characteristics in combination distinguish 'JINGFENG VARIEGATA' as a new and distinct *Hoya* cultivar:

1. Undulating foliage.
2. Glossy foliage.
3. Dark green foliage with large light yellow variegation on center of leaf.

PARENT COMPARISON

Plants of the new cultivar 'JINGFENG VARIEGATA' are similar to the seed parent in most horticultural characteristics. The new variety, however, differs in the following:

1. The new variety has more leaf undulation than the parent variety.
2. The new variety has more light yellow leaf variegation than the parent variety.

COMMERCIAL COMPARISON

'JINGFENG VARIEGATA' can be compared to compared to the commercial variety *Hoya* 'Krinkle Kurl', unpatented.

Plants of 'Krinkle Kurl' are similar to plants of 'JINGFENG VARIEGATA' in most horticultural characteristics, however, plants of 'JINGFENG VARIEGATA' differ in the following:

1. Plants of 'Krinkle Kurl' are significantly more compact than plants of the new variety.
2. Foliage of 'Krinkle Kurl' is very strongly undulate; foliage of the new variety is moderately undulate.
3. Foliage of 'Krinkle Kurl' is colored green with green-white variegation; foliage of the new variety is dark green with a light yellow center variegation.

BRIEF DESCRIPTION OF THE PHOTOGRAPHS

The accompanying drawings illustrate in full color various details of typical plants of 'JINGFENG VARIEGATA' grown in a greenhouse in Chuzhou, China. These plants are approximately 3 years old, shown in 10 cm pots. The photograph was taken using conventional techniques and although colors may appear different from actual colors due to light reflectance it is as accurate as possible by conventional photographic techniques.

DETAILED BOTANICAL DESCRIPTION

Figure 1:
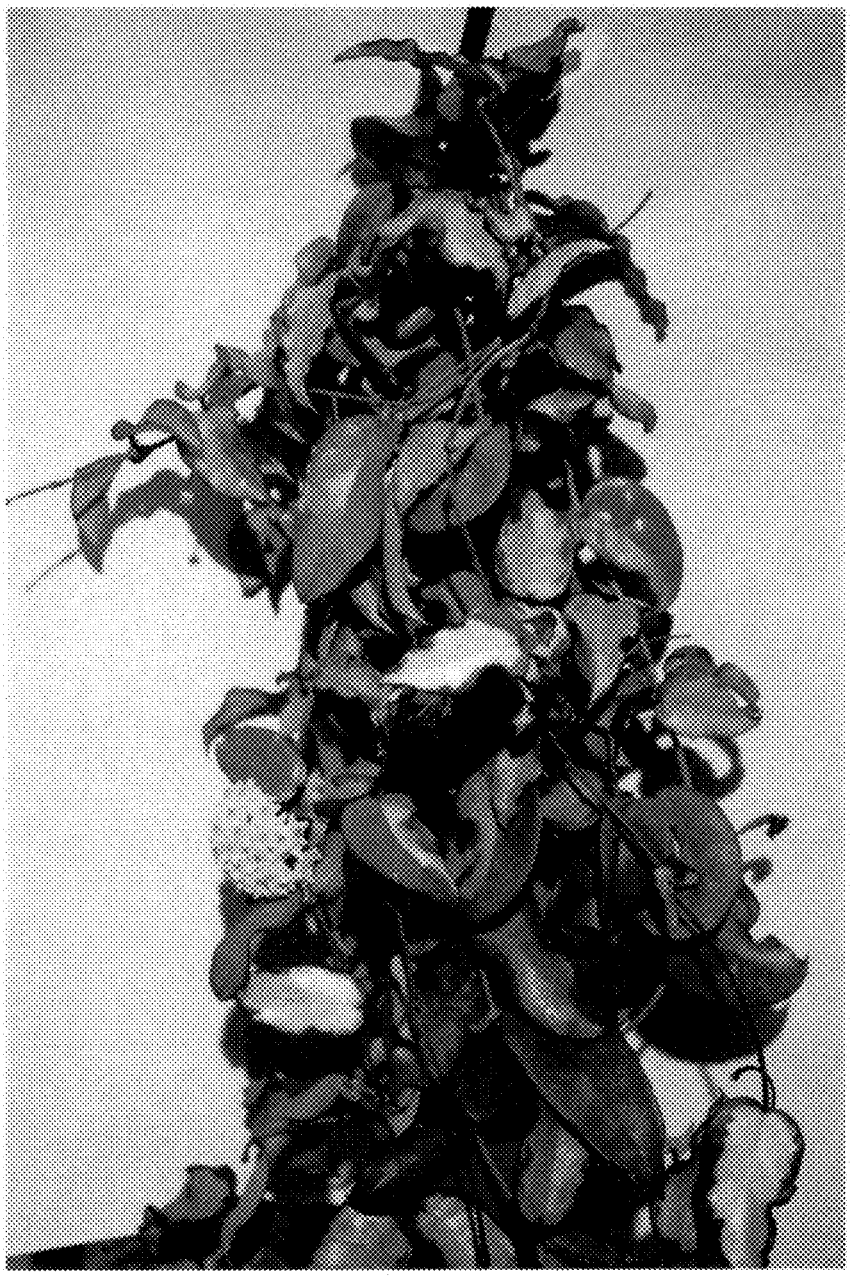
FIG. 1 illustrates a mature flowering plant of 'JINGFENG VARIEGATA'.
Figure 2:
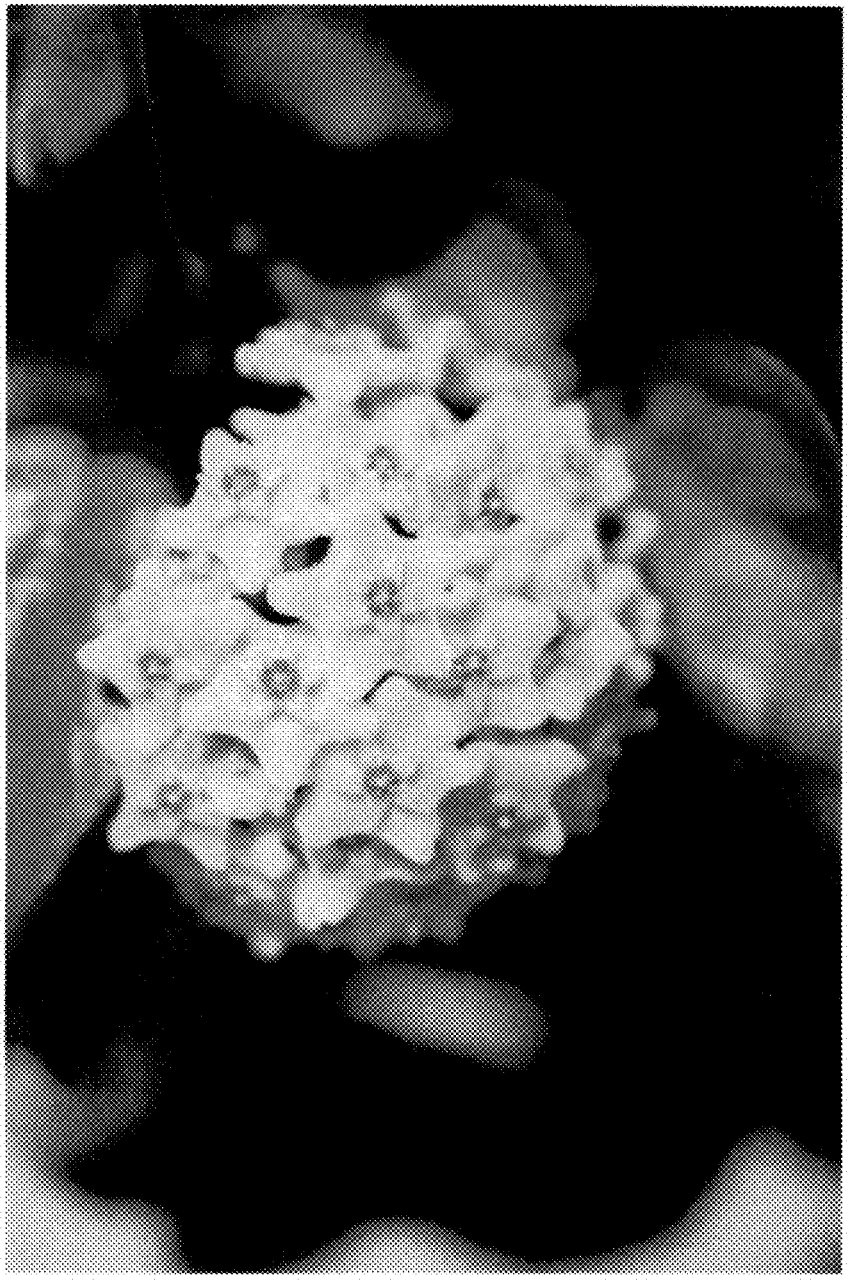
FIG. 2 illustrates a close-up view of the inflorescence of 'JINGFENG VARIEGATA'.
Figure 3:
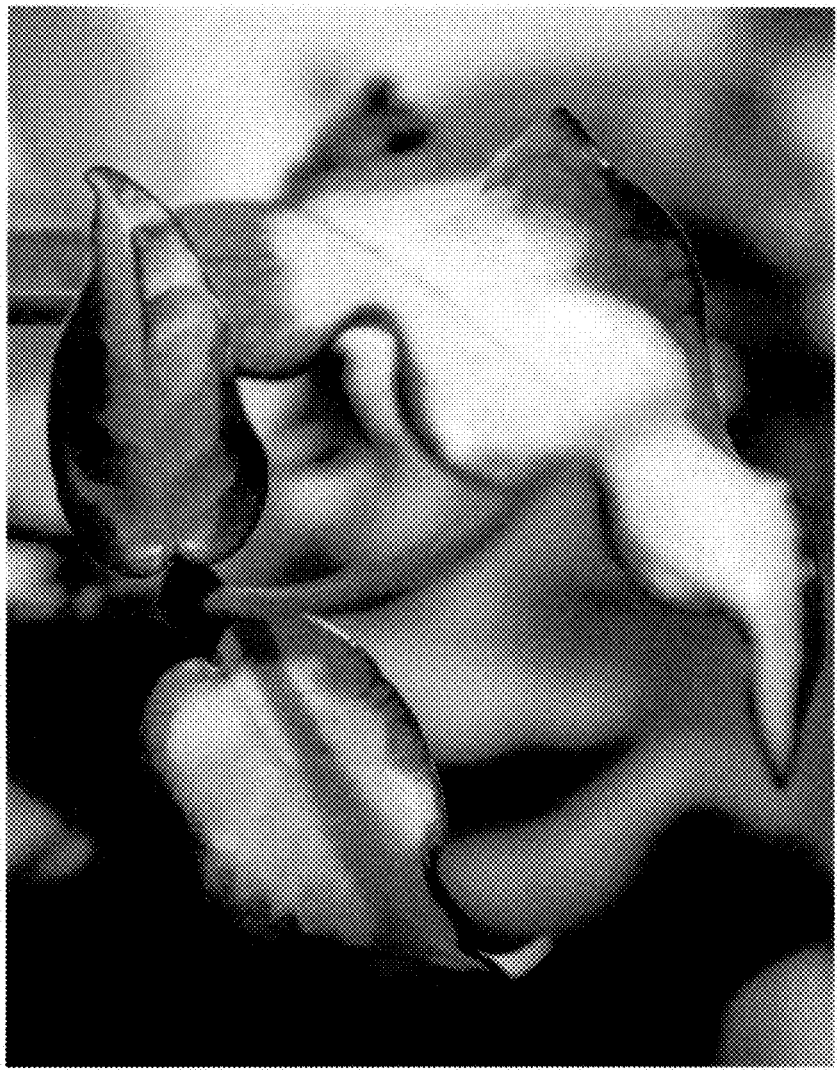
FIG. 3 illustrates a close-up view of the upper surface of foliage of 'JINGFENG VARIEGATA'.
Figure 4:
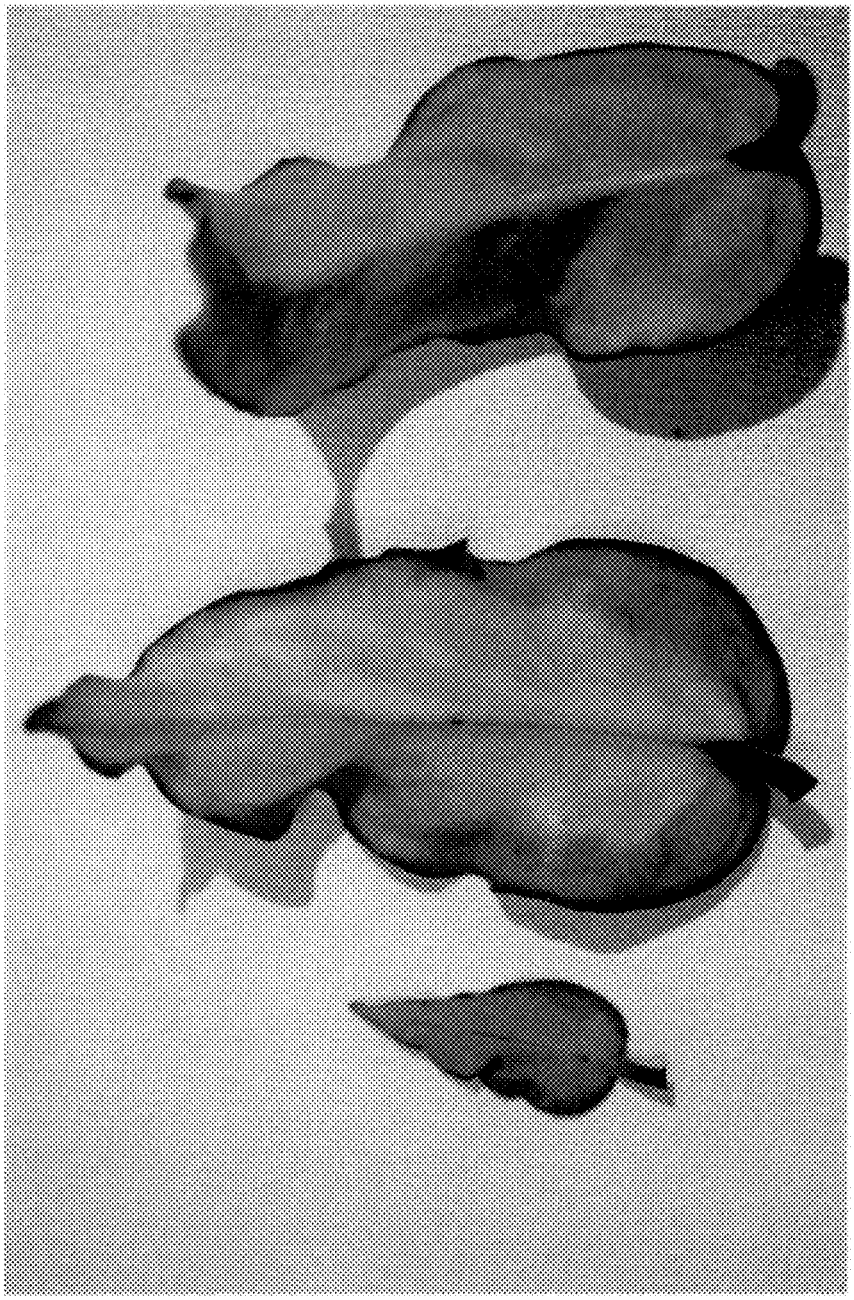
FIG. 4 illustrates a close-up view of the lower surface of foliage of 'JINGFENG VARIEGATA'.

In the following description, color references are made to The Royal Horticultural Society Colour Chart 2001, except where general terms of ordinary dictionary significance are used. The following observations and measurements describe 'JINGFENG VARIEGATA' plants grown in a greenhouse in Chuzhou, China. Temperatures ranged from 22° C. at night to 26° C.during the day. No artificial light, photoperiodic treatments were given to the plants. Measurements and numerical values represent averages of typical plant types.

Botanical classification: *Hoya commutata* 'Jingfeng Variegata'.

PROPAGATION

Time to initiate roots: About 15 days at approximately 30° C. in the summer. About 25 days at 18° C. in the winter.

Time to produce a rooted cutting: About 50 days at 20° to 30° C.

Root structure:
- *Shape.*—Beard.
- *Length.*—20 cm.
- *Diameter.*—0.1 cm.
- *Texture.*—Fleshy.
- *Color.*—RHS White 155B.

PLANT

Plant type: Perennial flowering vine.
Age of plant described: 3 years.
Container size: 10 to 15 cm.
Height: 58 cm.
Plant spread: 36 cm.
Growth rate: High.
Plant vigor: High.
Branching characteristics: Basal; no pinching required.
Length of primary lateral branches: Approximately 10 to 15 cm.
Diameter of lateral branches: Approximately 4 mm.
Internode length: 5.4 to 11.7 cm.
Stem texture: Matte, pubescent.
Color:
- *Developing.*—RHS Reddish-Brown 166B.
- *At Internodes.*—RHS Green 137B.
- *Developed.*—RHS Brown 199A.

FOLIAGE

Leaf:
- *Arrangement.*—Opposite, single.
- *Average length.*—6.4 to 10.8 cm.
- *Average width.*—3.4 to 5.8 cm.
- *Shape of blade.*—Narrow ovate.
- *Apex.*—Acute.
- *Base.*—Cordate.
- *Aspect.*—Moderately undulating.
- *Margin.*—Undulating. Entire.
- *Texture.*—Leathery, both surfaces.
- *Pubescence.*—Both sides covered with short, woolly hairs.
- *Rugosity.*—Smooth.
- *Luster.*—Upper Side: High. Under Side: Medium.
- *Color.*—Young Foliage, Upper Side: Narrow edge: RHS Yellow-Green 147A; center: Orange N167C. Young Foliage, Under Side: Narrow edge: RHS Yellow-Green 148B; center: Yellow-Green 145B. Mature Foliage, Upper Side: Narrow edge: RHS Green 137B; center: Yellow 10D. Mature Foliage, Under Side: Narrow edge: RHS Green 138B; center: Yellow-Green 150C. Autumn Foliage, Upper Side: Narrow edge: RHS Green 137B; center: Yellow 10D. Autumn Foliage, Under Side: Narrow edge: RHS Green 138B; center: Yellow-Green 150C.
- *Venation.*—Type: Pinnate. Color Upper Side: RHS Yellow-Green 145C. Color Under Side: RHS Yellow-Green 149A.
- *Petiole.*—Length: 1.1 to 1.6 cm. Diameter: 0.4 to 0.5 cm. Color, Upper Side: RHS Brown 200A. Color, Under Side: RHS Brown 200B. Texture: Fleshy. Luster: Weak. Strength: Medium.

FLOWER

Natural flowering season: February through December.
Flower arrangement: Cymose umbel.
Flower type and form: Hemispherical star shape.
Inflorescence type and form: Umbelliform.
Quantity of flowers: 30 to 50 per inflorescence; 10 to 20 per plant.
Flower longevity: 10 days.
Inflorescence size:
- *Diameter.*—5.8 cm.
- *Length.*—6.3 cm.

Bud:
- *Shape.*—Star.
- *Length.*—0.4 cm.
- *Diameter.*—1 cm.
- *Color.*—RHS Yellow-Pink 27C; Yellow 4D in center.
- *Texture.*—Waxy.
- *Luster.*—High.

Flower:
- *Shape.*—Star.
- *Height.*—2 cm.
- *Diameter.*—1.5 cm.
- *Length.*—0.3 cm.

Petals:
- *Arrangement.*—Double whorl.
- *Quantity.*—10 per flower.
- *Shape.*—Ovate.
- *Length.*—Corolla 0.8 cm; corona 0.3 cm.
- *Width.*—Corolla 0.6 cm; corona 0.2 cm.
- *Margin.*—Medium undulation.
- *Apex.*—Acute.
- *Base.*—Fused.
- *Texture, both sides.*—Corolla: fleshy; corona: leathery.
- *Rugosity, both sides.*—Corolla: pubescent; corona: waxy.
- *Luster, both sides.*—Corolla: weak; corona: high.
- *Color.*—When opening: Upper surface: Corolla: RHS Red 36D; Corona: Yellow 4D. Lower surface: Corolla: RHS Red 36D; Corona: Yellow 4D. Fully opened: Upper surface: Corolla: RHS Red 36D; Corona: Yellow 4D. Lower surface: Corolla: RHS Red 36D; Corona: Yellow 4D. Fading: Upper surface: Corolla: RHS Greyed-Orange N170A; Corona: White 155D. Lower surface: Corolla: RHS Greyed-Orange N170A; Corona: White 155D.

Sepals:
- *Arrangement.*—Single whorl.
- *Shape.*—Narrow ovate.
- *Quantity.*—5 per flower.
- *Length.*—0.4 cm.
- *Width.*—0.2 cm.
- *Margin.*—Entire.
- *Apex.*—Acute.
- *Base.*—Fused.

*Texture, both sides.*—Papery.
*Luster, upper side.*—High.
*Luster, under side.*—Weak.
*Color.*—When opening: Upper Surface: RHS Purple-Red 59A. Lower Surface: RHS Purple-Red 59B. Fully opened: Upper Surface: RHS Purple-Red 59A. Lower Surface: RHS Purple-Red 59B.

Calyx:
*Shape.*—Narrow ovate.
*Length.*—0.4 cm.
*Diameter.*—0.5 cm.

Peduncles:
*Length.*—3.5 cm.
*Width.*—0.2 cm.
*Angle.*—15° to 30°.
*Strength.*—Weak.
*Texture.*—Fleshy.
*Luster.*—Weak.
*Color.*—RHS Brown N200A.

Pedicels:
*Length.*—2.8 cm.
*Diameter.*—0.1 cm.
*Aspect.*—100° to 155°.
*Strength.*—Weak.
*Texture.*—Fleshy.
*Luster.*—Weak.
*Color.*—RHS Purple-Red 64D.

Fragrance: Moderate, sweet.

REPRODUCTIVE ORGANS

Stamens: Appressed to stigma, no distinguishable parts.

Pistil:
*Number.*—1.
*Length.*—0.1 cm.
*Style color.*—Near RHS Yellow-White 158B.
*Stigma.*—Shape: Oval. Color: White. N155B Ovary Color: RHS Orange-White 159C.

OTHER CHARACTERISTICS

Disease resistance: High resistance to normal diseases and pests of *Hoya* have been observed. Typical pests of *Hoya* include aphid(*Aphis nerii*), red spider mite(*Tetranychus tumidus*) and scale(*Coccus hesperidum*). The most common disease found in *Hoya*, in the inventor's experience is Anthracnose(*Colletotrichum* sp.).

Drought tolerance and cold tolerance: Tolerates temperatures from approximately 3° C. to 45° C. Moderate tolerance to rain. High tolerance to wind.

Fruit/seed production: Not observed.

What is claimed is:

1. A new and distinct cultivar of *Hoya* plant named 'JINGFENG VARIEGATA' as herein illustrated and described.

* * * * *